United States Patent [19]

Henry

[11] Patent Number: 5,037,408

[45] Date of Patent: Aug. 6, 1991

[54] OSTOMY BAG CLEANING METHOD AND APPARATUS

[75] Inventor: James S. Henry, Sarasota, Fla.

[73] Assignee: Arnold Technologies, Inc.

[21] Appl. No.: 537,610

[22] Filed: Jun. 14, 1990

[51] Int. Cl.⁵ .............................................. A61F 5/44
[52] U.S. Cl. ................................... 604/332; 604/334
[58] Field of Search .............................. 604/332–338, 604/277

[56] References Cited

U.S. PATENT DOCUMENTS

| | | | |
|---|---|---|---|
| 2,664,573 | 1/1954 | Taylor | 604/334 |
| 2,782,785 | 4/1955 | Arcand | 604/334 |
| 2,928,393 | 3/1960 | Marsen | 604/334 |
| 4,460,359 | 7/1984 | Fenton | 604/332 |
| 4,642,106 | 2/1987 | Downey | 604/332 |
| 4,654,037 | 3/1987 | Fenton | 604/334 |

Primary Examiner—Randall L. Green
Assistant Examiner—R. Clarke
Attorney, Agent, or Firm—William M. Hobby, III

[57] ABSTRACT

An ostomy bag cleaning method and apparatus for cleaning an ostomy bag which bag has a flexible bag portion with a stoma opening and a plurality of ostomy belt tabs each tab having an opening therein. The ostomy bag also has a drain opening and a closure for the drain opening. An ostomy bag cleaning tool includes a tool member having a pair of arms connected to each other at one end and an ostomy bag connector on the other end of each arm and shaped to fit into an ostomy bag belt holding tab opening for supporting the bag thereon. The ostomy bag connector can include the tip of each arm being formed in a generally U-shape with the tip of the U extending at a right angle away from the rest of the arm and having a resilient tip cover thereover. The method includes removing the ostomy bag from the patient, selecting the ostomy bag cleaning tool, inserting the ostomy bag support tool tips into the tab openings of the ostomy bag, ostomy belt tabs, removing the closure for the ostomy bag drain opening and supporting the ostomy bag within a toilet bowl with the ostomy bag stoma opening below the water level and flushing the toilet to thereby flush water through the ostomy bag for rapid cleansing.

5 Claims, 1 Drawing Sheet

U.S. Patent        Aug. 6, 1991        5,037,408

OSTOMY BAG CLEANING METHOD AND APPARATUS

BACKGROUND OF THE INVENTION

The present invention relates to a novel implement for and method of emptying the contents of a conventional ostomy bag and, more specifically, to a simple, manually manipulated instrument and method of use thereof in facilitating evacuation of the contents of an ostomy bag.

Surgical procedures providing substitute paths for evacuation of body wastes necessitated by removal or lack of function of basic elements of the gastrointestinal or urinary tracts have been successfully practiced for many years. For example, the two principal types of surgeries involving the intestinal tract are colostomy and ileostomy. A number of variants of these procedures, as well as other types of ostomy surgery are commonly performed, over one million Americans being ostomates and a large number of people in the United States undergo ostomy surgery each year.

The bowel waste and other effluent diverted through the colon to the surface of the abdomen is discharged through a surgically-created exit or "stoma" into a flexible bag or pouch having an opening communicating therewith. The cost of the pouches, and frequency with which they must be emptied and/or replaced, often makes it economically unfeasible to discard the pouches with each replacement. Thus, drainable pouches are conventionally used to permit emptying the contents through an opening in one end, remote from the stoma-communicating opening, into a suitable receptacle, whereby the pouch can be used through multiple emptying cycles.

The emptying of the pouch is performed manually, removing the clamp normally sealing the drainage opening and directing the effluent into a toilet or other receptacle. The pouch is usually squeezed manually and may be flushed with water to complete the emptying operation. The pouch, particularly the end having the drainage opening, is wiped with tissues and the clamp replaced. The procedure is almost always messy and disagreeable.

Prior U.S. patents which use tools to clean ostomy bags may be seen in the Downey U.S. Pat. No. 4,642,106 for an implement for a evacuating the contents of a drainable ostomy pouch and has connected arms which squeeze on the pouch and can be used to squeeze the contents out the drainage opening. The Arcand U.S. Pat. No. 2,782,785 is for a colostomy washing device for washing out a colostomy bag. The Marsan U.S. Pat. No. 2,928,393 is a colostomy appliance which provides for an insertion nozzle for cleaning the bag. The Voorhies patent is a kit for an ostomate which attaches a tube with a nozzle on the end thereof for insertion into an ostomy bag for spraying inside the ostomy bag for cleaning the bag. The Taylor U.S. Pat. No. 2,664,573 is an excrement disposal device which can be mounted adjacent a toilet and has an opening for connecting adjacent a patient's stoma opening. The Fenton U.S. Pat. No. 4,654,037 is an ostomy pouch irrigator which inserts a nozzle into an ostomy bag for spraying and cleaning the bag. The Fenton U.S. Pat. No. 4,460,359 is a clamp closure assembly for an ostomy bag.

SUMMARY OF THE INVENTION

An ostomy bag cleaning method and apparatus for cleaning an ostomy bag which bag has a flexible bag portion with a stoma opening and a plurality of ostomy belt tabs each tab having an opening therein. The ostomy bag also has a drain opening and a closure for the drain opening. An ostomy bag cleaning tool includes a tool member having a pair of arms connected to each other at one end and an ostomy bag connector on the other end of each arm and shaped to fit into an ostomy bag belt holding tab opening for supporting the bag thereon. The ostomy bag connector can include the tip of each arm being formed in a generally U-shape with the tip of the U extending at a right angle away from the rest of the arm and having a resilient tip cover thereover. The method includes removing the ostomy bag from the patient, selecting the ostomy bag cleaning tool, inserting the ostomy bag support tool tips into the tab opening of the ostomy bag, ostomy belt tabs, removing the closure for the ostomy bag drain opening and supporting the ostomy bag within a toilet bowl with the ostomy bag stoma opening below the water level and flushing the toilet to thereby flush water through the ostomy bag for rapid cleansing.

BRIEF DESCRIPTION OF THE DRAWINGS

Other objects, features, and advantages of the present invention will be apparent from the written description and the drawings in which.

DETAILED DESCRIPTION OF THE PREFERRED EMBODIMENT

Figure 1:
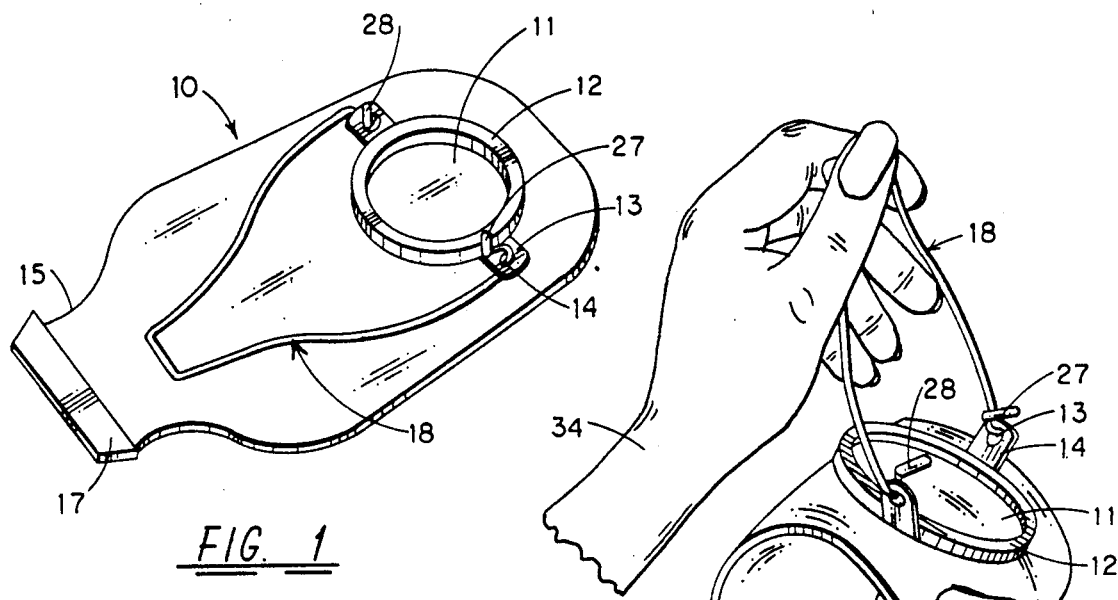
FIG. 1 is a perspective view of an ostomy bag having a tool attached thereto.

Referring to the drawings, an ostomy bag 10 is illustrated having a stoma opening 11 with a ostomy bag retainer ring 12 therearound and having a pair of support belt tabs 13 mounted on each side of the retainer ring 11 and each tab 13 having an aperture 14 therethrough for attaching an ostomy bag support belt which wraps around the patient to provide additional support to the ostomy bag 10 when attached to a patient's stoma opening. The ostomy bag 10 also has a narrow end portion 15 having a cleanout or drain opening 16 having a seal or clamp member 17 attached thereover.

Figure 4:
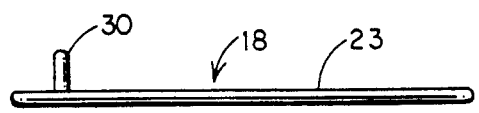
FIG. 4 is a side elevation of the ostomy bag cleaning tool of FIGS. 1–3.
Figure 5:
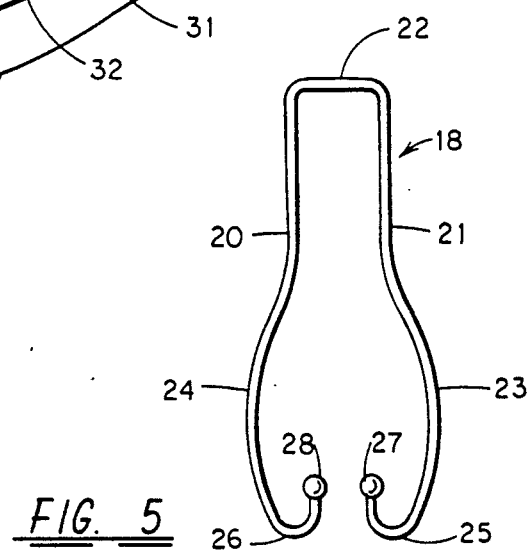
FIG. 5 is a top elevation of an ostomy bag cleaning tool in accordance with FIGS. 1–4.

In FIG. 1, an ostomy bag support and cleaning tool 18 has a pair of arms 20 and 21 connected together by bar 22 and in which the arms 20 and 21 and bar 22 are formed of one piece of elongated metal, such as stainless steel or the like. The arms 20 and 21 expand into an arcuate shape 23 for arm 21 and shape 24 for arm 20 and then forms a generally U-shaped end portion 25 of arm 21 and U-shaped end portion 26 for arm 20. The U-shaped end portion 25 has the tip 27 at a generally right angle to the arm 21 while the tip 28 at the end of the arm 20 is also at a right angle to the arm 20. The tips 27 and 28 each have a soft vinyl rubber resilient tip 30 mounted over the end thereof. Thus, the tool as shown in FIGS. 4 and 5 is a generally tonged shaped tool having specially shaped ostomy bag connecting tip portions formed such that the arms 20 and 21 can be spread apart or brought together to change the position of connecting tips 27, 28 for any of plurality of different size ostomy bags.

Figure 2:
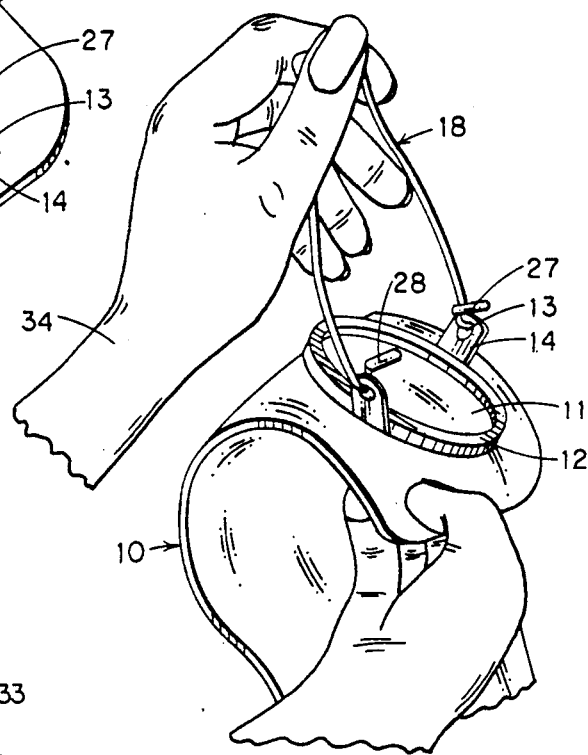
FIG. 2 is a perspective view of the opening of the ostomy bag with the tool attached thereto.
Figure 3:
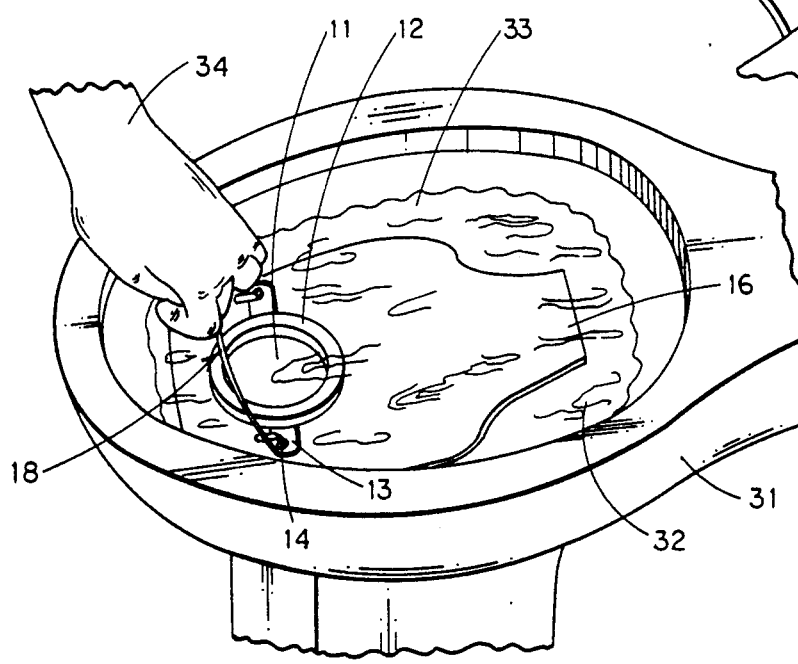
FIG. 3 is a perspective view of a toilet bowl having the ostomy bag supported therein by the tool.

In operation, the tool and method are used, as shown in FIGS. 1-3, in which the ostomy bag 10 is removed from the patient having the drain opening seal 17 in place. The ostomy cleaning tool 18 arms are spread apart as shown in FIG. 18 and the connecting tips 27 and 28 are inserted through the apertures 14 of the tabs 13 on either side of the ostomy pouch retainer ring 12 and onto the U-shaped portions 25 and 26. The ostomy bag can then be lifted as shown in FIG. 2 and the drain seal 17 removed from the drain opening. The ostomy pouch is then lowered into a toilet 31, toilet bowl 32 which is partially filled with water 33 until the bag stoma opening 11 is below the water level of the water 32. A patient's hand 34 grips the bar 22 to hold the bag in position while flushing the toilet 31. Water is then pulled during the flushing operation through the opening 11 through the ostomy bag 10 and out the drain opening 16 which may be pulled down into the siphon opening of the toilet as the water is flushed through. The bag is thereby thoroughly cleaned and can be removed and attached to the patient.

The method comprises removing a used ostomy bag from a patient and selecting an ostomy bag support tool 18 having a pair of arms 20 and 21 and connecting tips 27 and 28 and inserting the ostomy bag support tool 18, tips 27 and 28 into the tab 13 openings 14 of the ostomy bag, ostomy support belt tabs and removing the closure or seal 17 from the ostomy bag drain opening 16. Finally, the ostomy bag is supported within a toilet bowl with the ostomy bag stoma opening below water level in the toilet bowl, then flushing the toilet with the ostomy bag therein so that the ostomy bag is flushed by water passing therethrough.

It should be clear at this time that an ostomy bag supporting and cleaning tool and an ostomy bag cleaning method have been provided which provides a single piece tong tool with ostomy bag supporting tips thereon and which provides a convenient method for cleaning the ostomy bag in a toilet bowl without the patient having to use a special nozzle and flushing systems. However, the present invention should not be construed as limited to the forms shown which are to be considered illustrative rather than restrictive.

I claim:

1. An ostomy bag cleaning method for cleaning an ostomy bag having a flexible bag with a stoma opening, a plurality of ostomy belt tabs, each tab having an opening therein, said ostomy bag also having a drain opening and a closure for the drain opening, said method comprising the steps of:

removing a used ostomy bag from a patient;
   selecting an ostomy bag support tool having a pair of arms connected to each other on one end and the other end of each of said arms having a tip shaped for insertion into the belt opening of said ostomy bag belt tabs;
   inserting said ostomy bag support tool tips into the tab opening for said ostomy bag ostomy belt;
   removing the closure for said ostomy bag drain opening from said opening;
   supporting said ostomy bag with said ostomy bag support tool in a toilet bowl with the ostomy bag stoma opening below water level in said toilet bowl; and
   flushing said toilet with said ostomy bag therein whereby said ostomy bag is flushed by water passing therethrough.

2. An ostomy bag cleaning method for cleaning an ostomy bag in accordance with claim 1 in which the step of selecting an ostomy bag support tool includes selecting a tool having both arms formed from one piece of material.

3. An ostomy bag cleaning method for cleaning an ostomy bag in accordance with claim 2 in which the step of selecting an ostomy bag support tool includes selecting a tool in which each arm has a right angle tip for insertion into the ostomy bag belt tab opening.

4. An ostomy bag cleaning method for cleaning an ostomy bag in accordance with claim 3 in which the step of selecting an ostomy bag support tool includes selecting a tool having a generally U-shaped end portion and the end of said U-shaped has said right angle tip protruding therefrom.

5. An ostomy bag cleaning method for cleaning an ostomy bag in accordance with claim 4 in which the step of selecting an ostomy bag support tool includes selecting a tool having resilient covers over said arm right angle tip protruding therefrom.

* * * * *